(12) United States Patent
Russ et al.

(10) Patent No.: US 7,341,743 B2
(45) Date of Patent: Mar. 11, 2008

(54) COLOR COSMETIC COMPOSITIONS

(75) Inventors: Julio Gans Russ, Westfield, NJ (US); Ida Marie Sandewicz, Monroe Township, NJ (US); Tatyana Zamyatin, Princeton Junction, NJ (US); Merry Lee Nickl, Kingston, NJ (US)

(73) Assignee: Revlon Consumer Products Corporation, New York, NY (US)

( * ) Notice: Subject to any disclaimer, the term of this patent is extended or adjusted under 35 U.S.C. 154(b) by 0 days.

(21) Appl. No.: 11/249,882

(22) Filed: Oct. 13, 2005

(65) Prior Publication Data

US 2006/0093564 A1 May 4, 2006

Related U.S. Application Data

(60) Provisional application No. 60/622,825, filed on Oct. 28, 2004.

(51) Int. Cl.
- *A61K 9/14* (2006.01)
- *A61K 9/16* (2006.01)
- *A61K 7/00* (2006.01)
- *A61K 33/26* (2006.01)

(52) U.S. Cl. .................. 424/489; 424/401; 424/490; 424/646

(58) Field of Classification Search ............ 424/401, 424/489, 490, 64, 70.7, 646
See application file for complete search history.

(56) References Cited

U.S. PATENT DOCUMENTS

| | | | |
|---|---|---|---|
| 3,393,155 A | 7/1968 | Schutte | 252/316 |
| 3,691,090 A * | 9/1972 | Kitajima et al. | 427/213.36 |
| 4,777,035 A | 10/1988 | Shin | 424/66 |
| 6,126,926 A | 10/2000 | Tanaka | 424/62 |
| 6,207,175 B1 | 3/2001 | Lebreton | 424/401 |
| 6,290,941 B1 | 9/2001 | Lahanas | 424/69 |
| 6,413,548 B1 | 7/2002 | Hamer | 424/489 |
| 6,458,372 B1 | 10/2002 | Scodamaglia-Crockett | 424/401 |
| 6,461,621 B1 | 10/2002 | Gagnebien | 424/401 |
| 6,497,891 B2 | 12/2002 | Bara | 424/401 |
| 2003/0180235 A1 | 9/2003 | Grisoni | 424/59 |
| 2004/0028710 A1 | 2/2004 | Oka | 424/401 |
| 2004/0265348 A1 * | 12/2004 | Hollenberg et al. | 424/401 |

FOREIGN PATENT DOCUMENTS

| | | |
|---|---|---|
| EP | 1206928 | 5/2002 |
| JP | 2000309595 | 11/2000 |
| JP | 2002265388 | 9/2002 |
| JP | 2003267826 | 9/2003 |

OTHER PUBLICATIONS

LCW—Sensient Cosmetic Technologies, Technical Bulletin. Serica 5 Covasil 4-05. Feb. 4, 1998.
LCW—Sensient Cosmetic Technologies, Specification Sheet. Cardre Talc FHC. Jan. 1, 2001.
LCW—Sensient Cosmetic Technologies, Technical Bulletin, Covabead LH 85. Sep. 8, 1998.
LCW-Sensient Cosmetic Technologies, Technical Bulletin, Talc Covasil 4-05. Mar. 19, 1998.
LCW-Sensient Cosmetic Technologies, Technical Bulleting, Covagel. Jan. 1, 2000.
Alusion. Aluminum Soft Focus Powder (AL 5-10). Jan. 1, 2001.
Related U.S. Appl. No. 10/914,571, filed Jul. 12, 2004, entitled: Packaged Cosmetic Compositions and Related Methods.
U.S. Appl. No. 10/914,571, filed Jul. 12, 2004. Packaged Cosmetic Compositions and Related Methods.
U.S. Appl. No. 10/955,076, filed Sep. 30, 2004. Color Cosmetic Compositions.
U.S. Appl. No. 11/017,278, filed Dec. 20, 2004. Antiperspirant/Deodorant Compositions and Methods.
Volu Lips Active Powder. Circa Dec. 2005.
DeGussa. Product Information. Aerosil R202. Mar. 2004.
Cabot. Cab-O-Sil Fumed Silica in Cosmetic and Personal Care Products. Sep. 2004.
Kobo Products, Inc. Aqua Keep. Jan. 2003.
Kobo. Product Specifications. Aqua Keep 10SH-NF. Nov. 2004.
DeGussa. Technical Information. No. 1270. Dry Water—Aqueous Media in Powder Form. Mar. 2005.

* cited by examiner

*Primary Examiner*—Johann R. Richter
*Assistant Examiner*—Konata M. George
(74) *Attorney, Agent, or Firm*—Jay S. Goudie

(57) ABSTRACT

A color cosmetic composition containing color impregnated spherules where the color is expressed from the spherule upon application of the cosmetic to the keratinous surface and the expressed spherule serves an uptake function on the keratinous surface; a cosmetic composition containing a rupturable spherule filled with color, and a method for color skin using such compositions.

1 Claim, No Drawings

COLOR COSMETIC COMPOSITIONS

RELATED APPLICATIONS

This application claims priority to provisional patent application Ser. No. 60/622,825, filed Oct. 28, 2004.

TECHNICAL FIELD

The invention is in the field of cosmetic compositions, particularly color cosmetic compositions such as lipsticks, lip glosses, blushers, eyeshadows, mascara, concealer, and the like.

BACKGROUND OF THE INVENTION

Cosmetic manufacturers are on an eternal quest to provide color cosmetic products that provide multiple benefits. For example, it is desirable for a single cosmetic to be suitable for all skin types: dry, oily, or combination; and exhibit desirable properties such as long wear or transfer resistance that look freshly applied all day. Today's women lead busy lives and do not have time or inclination to reapply cosmetics during the day. Most consumers desire color cosmetics that will stay on the skin or lips, for example, for at least eight hours, so that when they apply make up in the morning it will stay on their face throughout the work day. Such consumers are also interested in products that are suitable for the multiplicity of skin conditions they must contend with throughout the year. For example, perhaps a consumer has oily skin during the warm summer months and is interested in a foundation that is less oily, or even capable of absorbing sebum. However, when the cold winter months arrive, this same consumer's skin becomes dry and that same "summer" makeup is no longer the best choice. The consumer then grudgingly tries to find another foundation product more suitable for use in the winter months and may even become confused by the plethora of product offerings in stores. In this case a makeup suitable for use across all four seasons would be the best all around choice for such a consumer. Or another consumer may want a foundation makeup that has the qualities desirable in a "sport" makeup, that is a makeup that is long wearing and absorptive when the consumer is engaging in sporting activities or exercising. At the same time that same makeup should be suitable for wearing to the office on a typical work day. In addition to being more convenient for consumers, this approach is most advantageous for the cosmetic manufacturer as well. More SKU's mean more financial support in terms of maintenance, advertising, packaging and the like. Fewer SKUS with more sales associated with them are always more profitable for the cosmetic manufacturer.

Accordingly, there is a need for color cosmetic products that are multi-benefit, or suitable for use with different types of skin conditions, and that may adapt themselves to skin conditions as they occur.

It is an object of the invention to provide color cosmetic compositions that have one or more ingredients that have multiple functionalities.

It is further object of the invention to provide transfer resistant and/or long wearing color cosmetic compositions such as lip color, eye color, mascara, foundation, blush, concealer, and the like.

It is a further object of the invention to provide color cosmetic compositions wherein at least a portion of the color is contained in a spherule where the color is expressed from the cavities upon application of pressure when the cosmetic composition is applied, and wherein the emptied spherule shell is capable of imbibing sebum, perspiration, and the like as the color cosmetic is worn throughout the day.

It is an object of the invention to provide a color cosmetic composition containing color impregnated spherules where the color is expressed from the spherule upon application to the keratinous surface and the expressed spherule remains on the skin and has an uptake function.

It is an object of the invention to provide transfer resistant and/or long wearing color cosmetic compositions such as lip color, eye color, mascara, foundation, blush, concealer, and the like.

SUMMARY OF THE INVENTION

The invention is directed to a color cosmetic composition containing color impregnated spherules where the color is expressed from the spherule upon application of the cosmetic to the keratinous surface and the expressed spherule serves an uptake function on the keratinous surface.

The invention is further directed to a color cosmetic composition containing rupturable synthetic thermoplastic spherules impregnated with color.

The invention is further directed to a method for applying color to skin comprising treating the skin with a cosmetic composition containing color impregnated spherules which express color onto the skin when the composition is applied thereto.

DETAILED DESCRIPTION

I. Definitions

A. All percentages mentioned herein are percentages by weight unless otherwise indicated.

B. The term "transfer resistant" when used with respect to cosmetic compositions, means a composition that, when applied to the desired keratinous surface, does not readily transfer to a tissue or other keratinous surface when the tissue or other keratinous surface is touched to the keratinous surface to which the cosmetic is applied.

C. The term "spherule" means a capsule or the like which has a hollow interior cavity or cavities capable of containing color. A spherule may be round with a single hollow interior single cavity or chamber, or it may be in other shapes. A spherule may also be a particulate having a sponge-like inner network with interstices or channels either within the inner area of the sphere. The interstices or channels may be interconnected, and may terminate on the surface of the spherule in the form of pores.

D. The term "impregnated" with respect to the color in the spherule, means that the color resides within the hollow interior cavity or cavities of the spherule.

E. The term "expressed" means, with respect to the spherule, that when the composition containing the spherule is applied to the skin the color impregnated within the spherule, at least in part, exudes from the spherule onto the skin.

F. The term "uptake function" means, with respect to the spherule, that after the color impregnated within the spherule is expressed when the composition containing the spherule is applied to the skin, the emptied spherule may serve as a so-called collection device for skin exudates such as sebum or perspiration. In other words, such skin exudates may be absorbed into the empty spherule providing a composition that has end benefit properties like sebum absorption, sweat resistance, and so on.

II. The Composition

A. Spherule

The spherule used in the compositions of the invention may be made from polymers, natural substances such as polysaccharides or hydrocolloids such as starch, algin, alginate, agar, agarose, pectin, polypectate, or carrageenan; proteins such as gelatin, casein, zein, soy, and albumin; fats and fatty acids such as mono-, di- and triglycerides, and lauric, capric, palmitic and stearic acid and their salts; Cellulosic derivatives such as methyl- and ethyl-cellulose and carboxylmethylcellulose; hydrophilic and lipophilic waxes such as shellac, PEG (polyethylene glycol), or carnauba wax or beeswax; sugar derivatives; and the like. The spherules are present in the composition ranging from 0.01-90%, preferably from about 0.1-85%, more preferably from about 0.5-85% by weight of the total composition.

The spherules may be manufactured according to methods well known in the art, including, but not limited to, coacervation, spray drying, co-extrusion, phase separation, gelation, spinning disk, phase separation, and the like.

In one case, the spherule may be prepared by combining the colorant with the material used to make the spherule and, in the case where the spherule is a polymer, polymerizing the monomers to provide a polymeric capsule containing the colorant impregnated within. Typically the spherule may comprise from about 0.1-99%, preferably from 0.5-85%, more preferably from 1-75% by weight of the total spherule of spherule shell material and from about 0.1-99%, preferably from about 0.5-85%, more preferably from about 1-75% by weight of the total spherule of colorant.

Particularly preferred is where the spherule is a thermoplastic polymer comprised of monomer units such as acrylic acid, methacrylic acid, or their simple $C_{1-12}$ esters, styrene, alkylenes (such as ethylene, propylene, butylene), or substituted alkylenes where the substituents are such as hydroxy, halogen, cyano, $C_{1-12}$ alkyl or alkoxy, and the like. Particularly preferred is where the spherule comprises a copolymer of methacrylic acid esters, alkylenes, substituted alkylenes, or mixtures thereof. More preferred is where the spherule comprises a copolymer of methyl methacrylate, acrylonitrile, and methyl methacrylate. A spherule having this composition that is impregnated with color may be purchased from Lipo Chemical under the tradename LIPO ADS, and has the INCI name acrylonitrile-methacrylonitrile-methyl methacrylate copolymer and iron oxides.

B. Colorant

The cosmetic compositions of the invention are colored. At least some of the colorant is impregnated within the spherule. The composition may additionally contain colorants and particulate fillers that are not impregnated into the spherule. In the event the colorant composition (the "load") found within the spherule is solvated or dispersed in a polar or nonpolar liquid or semi-solid, the general composition of the load may range from about 0.01-99% colorant and from about 0.01-99% nonpolar liquid or semi-solid, all percentages by weight of the total load composition.

The colorants that are impregnated into the spherule may be organic pigments, inorganic pigments or mixtures thereof, and they may be dispersed in the spherule as is, or solvated or dispersed in a liquid or semi-solid carrier that is impregnated in the spherule. The organic pigments that may be used are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes.

Suitable inorganic pigments include iron oxides, ultramarines, chromium, chromium hydroxide colors, and mixtures thereof.

The colorant may be dispersed or solvating in a polar or non-polar liquid or semi-solid. Examples of polar liquids suitable for dispersing or solvating the colorant include water, mono-, di-, or polyhydric alcohols, glycerine, sugars, and the like. Examples of nonpolar liquids suitable for solvating or dispersing the colorant may be paraffinic hydrocarbons, silicone oils, esters, and the like.

Particularly preferred is where the colorant comprises one or more iron oxides and is dispersed or solvated, preferably solvated, in water.

C. Other Ingredients

The compositions of the invention may include one or more additional ingredients are further described herein. The compositions of the invention may be in the anhydrous form, or in the form of emulsions or solutions containing water.

1. Water

In the case where the compositions of the invention are in the aqueous solution or water and oil emulsion form, the composition comprises from about 0.1-99%, preferably about 0.5-90%, more preferably about 1-80% by weight of the total composition of water.

2. Polar Solvents

The compositions may comprise one or more polar solvents besides water (in addition to those found in the spherule), that are generally soluble in the water to form a water phase in the case of emulsion or solution compositions. The polar solvents may also be present if the composition is in the anhydrous form. If present, such polar solvents may range from about 0.001-85%, preferably about 0.01-75%, more preferably about 0.1-65% by weight of the total composition. Suitable polar solvents include mono-, di-, or polyhydric alcohols including those having the general formula R—OH wherein R is a $C_{1-10}$ straight or branched: chain alkyl that may be substituted with one or more hydroxyl groups. Also suitable are short chain ($C_{1-4}$) alkylene glycols. Examples of such alcohols include ethanol, isopropanol, glycerin, butylene glycol, propylene glycol, and mixtures thereof. Suitable alkylene glycols include propylene, ethylene, or butylene glycols and the like.

3. Oils

The compositions of the invention preferably contain one or more oily ingredients. The term "oil" when used herein means an ingredient that is a pourable liquid at room temperature. Such oils tend to be generally nonpolar, but may contain substituents or moieties that are polar in character. The oils that may be used in the compositions of the invention are silicone oils, organic oils, or mixtures thereof. Such oils may be present ranging from about 0.1-98%, preferably 0.5-90%, more preferably about 1-80% by weight of the total composition. Such oils include, but are not limited to, those set forth herein.

(a). Silicone Oils

Silicone oils that may be used in the composition are volatile or non-volatile. The term "volatile" when used herein, means that the silicone oil has a vapor pressure of at least about 2 mm. of mercury at 20° C. The term "non-volatile" means that the oil has a vapor pressure of less than about 2 mm. of mercury at 20° C.

(i). Volatile Silicone Oils

Suitable volatile silicones include linear or cyclic volatile silicones. Suitable volatile silicone oils generally have a viscosity ranging from about 0.1 to 10, preferably about 0.1-5 centipoise at 25° C.

Cyclic silicones (or cyclomethicones) are of the general formula:

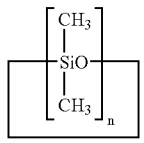

where n=3-6.

Linear volatile silicones in accordance with the invention have the general formula:

$(CH_3)_3Si-O-[Si(CH_3)_2-O]_n-Si(CH_3)_3$ where n=0, 1, 2, 3, 4, 5, 6, or 7, preferably 0, 1, 2, 3, 4, or 5, more preferably 1, 2, 3, or 4.

Linear and cyclic volatile silicones are available from various commercial sources including Dow Corning Corporation and General Electric. The Dow Corning volatile silicones are sold under the tradenames Dow Corning 244, 245, 344, and 200 fluids. These linear and cyclic volatile fluids include hexamethyldisiloxane, octamethylcyclotetrasiloxane, octamethyltrisiloxane, decamethyltetrasiloxane, decamethylcyclopentasiloxane, dodecamethylcyclohexasiloxane, and mixtures thereof.

(b). Hydrocarbon Oils

Also suitable are various straight or branched chain hydrocarbon oils that may be volatile or non-volatile.

(i). Volatile Hydrocarbon Oils

For example, suitable volatile hydrocarbons include straight or branched chain paraffinic hydrocarbons that may have from 5 to 20 carbon atoms, more preferably 8-19 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight ranging from about 70 to 225, preferably about 160 to 190, and a boiling point range of about 30 to 320, preferably about 60 to 260° C., and a viscosity of less than about 10 centipoise at 25° C. Such paraffinic hydrocarbons are available from EXXON under the ISOPARS trademark, and from the Permethyl Corporation. Suitable $C_{12}$ isoparaffins having the INCI name isododecane are manufactured by Permethyl Corporation under the tradename Permethyl 99A. Various $C_{16}$ isoparaffins commercially available under the trade name Permethyl R and having the INCI name isohexadecane are also suitable. Another suitable type of suitable paraffin is referred to as C9-11 isoparaffins, which is a mixture of isoparaffinic hydrocarbons having 9, 10, and 11 carbon atoms or C8-9 isoparaffins, which are a mixture of isoparaffinic hydrocarbons having 8 and 9 carbon atoms.

(ii). Non-Volatile Hydrocarbon Oils

Also suitable are various non-volatile hydrocarbon oils including isoparaffins and olefins, such as polyalphaolefins, having greater than 20 carbon atoms. Examples of such hydrocarbon oils include $C_{24-28}$ olefins, $C_{30-45}$ olefins, $C_{20-40}$ isoparaffins, hydrogenated polyisobutene, hydrogenated polydecene, polybutene, mineral oil, pentahydrosqualene, squalene, squalane, and mixtures thereof. Preferably such hydrocarbons have from greater than 20 to about 80 carbon atoms.

(c). Esters

Also suitable are various esters that may be in the form of mono-, di-, or triesters. Preferably, such esters have a viscosity ranging from about 10 to 1,000,000 centipoise at 25° C.

(i). Monoesters

Monoesters are generally formed by the reaction of a monocarboxylic acid having the formula R—COOH, wherein R is a straight or branched chain saturated or unsaturated alkyl having from 1 to 30 carbon atoms, or phenyl; and an alcohol having the formula R—OH wherein R is a straight or branched chain saturated or unsaturated alkyl having from about 1-30 carbon atoms, or phenyl. Both the alcohol and the acid may be substituted with one or more hydroxyl groups, and the carboxylic acid may be an alpha hydroxy acid. Either one or both of the acid or alcohol may be a "fatty" acid or alcohol, for example, may have from about 6 to 22 carbon atoms. Examples of monoester oils that may be used in the compositions of the invention include, but are not limited to, hexyldecyl benzoate, hexyl laurate, hexadecyl isostearate, hexydecyl laurate, hexyldecyl octanoate, hexyldecyl oleate, hexyldecyl palmitate, hexyldecyl stearate, hexyldodecyl salicylate, hexyl isostearate, butyl acetate, butyl isostearate, butyl oleate, butyl octyl oleate, cetyl palmitate, ceyl octanoate, cetyl laurate, cetyl lactate, isostearyl isononanoate, isononyl isononanoate, cetyl isononanoate, cetyl stearate, stearyl lactate, stearyl octanoate, stearyl heptanoate, stearyl stearate, and so on.

(ii). Diesters

Suitable diesters that may be used in the compositions of the invention are the reaction product of a dicarboxylic acid and an aliphatic or aromatic alcohol, or a monocarboxylic acid and an aliphatic or aromatic alcohol containing at least two hydroxyl groups. The dicarboxylic acid may contain from 1 to 30 carbon atoms, and may be in the straight or branched chain, saturated or unsaturated form. The dicarboxylic acid may be substituted with one or more hydroxyl groups. The aliphatic or aromatic alcohol may also contain 1 to 30 carbon atoms, and may be in the straight or branched chain, saturated, or unsaturated form. The aliphatic or aromatic alcohol may be substituted with one or more substituents such as hydroxyl. Preferably, one or more of the acid or alcohol is a fatty acid or alcohol, i.e. contains 6-22 carbon atoms. The dicarboxylic acid may also be an alpha hydroxy acid. Examples of diester oils that may be used in the compositions of the invention include diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisostearyl dimer dilinoleate, disostearyl fumarate, diisostearyl malate, isononyl isononanaote, isohexadecyl stearate, and so on.

(iii). Triesters

Suitable triesters comprise the reaction product of a tricarboxylic acid and an aliphatic or aromatic alcohol, or the reaction of an aliphatic or aromatic alcohol having three or more hydroxyl groups with mono- or dicarboxylic acids. As with the mono- and diesters mentioned above, the acid and alcohol contain from 1 to 30 carbon atoms, and may be saturated or unsaturated, straight or branched chain, and may be substituted with one or more hydroxyl groups. Preferably, one or more of the acid or alcohol is a fatty acid or alcohol containing 6 to 22 carbon atoms. Examples of triesters include triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate, tridecyl cocoate, tridecyl isononanoate, and so on.

(d). Lanolin Oil

Also suitable for use in the composition is lanolin oil or derivatives thereof containing hydroxyl, alkyl, or acetyl groups, such as hydroxylated lanolin, isobutylated lanolin oil, acetylated lanolin, acetylated lanolin alcohol, and so on.

(e). Glyceryl Esters of Fatty Acids

Also suitable for use as the oil are various synthetic or naturally occuring glyceryl esters of fatty acids, or triglycerides. Both vegetable, animal, or synthetic sources may be used. Examples of such oils include castor oil, $C_{10-18}$ triglycerides, caprylic/capric/triglycerides, coconut oil, corn oil, cottonseed oil, linseed oil, mink oil, olive oil, palm oil, illipe butter, rapeseed oil, soybean oil, sunflower seed oil, walnut oil, and the like.

4. Particulates

When the compositions of the invention are colored or opaque they may contain amounts of particulates ranging from about 0.01-95%, more preferably about 0.5-18% of particulate matter having a particle size of 0.01 to 200, preferably 0.25-100 microns. The particulate matter may be colored or non-colored (for example white) non-pigmentitious powders that may give the composition an opaque or semi-opaque quality. Suitable non-pigmentitious powders include bismuth oxychloride, titanated mica, fumed silica, spherical silica, polymethylmethacrylate, micronized teflon, boron nitride, acrylate copolymers, aluminum silicate, aluminum starch octenylsuccinate, calcium silicate, cellulose, chalk, corn starch, glyceryl starch, hydrated silica, kaolin, maltodextrin, microcrystalline cellulose, rice starch, silica, talc, mica, titanium dioxide, zinc laurate, zinc myristate, zinc rosinate, alumina, calcium carbonate, dextran, nylon, silica silylate, silk powder, sericite, soy flour, tin oxide, titanium hydroxide, trimagnesium phosphate, walnut shell powder, or mixtures thereof. While titanium dioxide is commonly considered to be a white pigment when used in paints, in cosmetics it is used more for its ability to mute color, and/or provide an opaque or semi-opaque finish, then as a colorizing ingredient. The above mentioned powders may be surface treated with lecithin, amino acids, mineral oil, silicone, or various other agents either alone or in combination, which coat the powder surface and render the particles more lipophilic in nature. In some cases the particulates may be in the form of fibers, which have a cross-sectional shape and some degree of length which may range from 0.1 mm. or greater. The particulates may also be in the lamellar, spherical, or other forms. Examples of particulates in lamellar form include mica and similar types of particulates that are found in sheet or platelet form. Examples of particulates in spherical form including spherical silica, and the like. Examples of such fibers include silk, nylon, cellulose, rayon, teflon, and other types of synthetic or natural materials.

The particulate matter component also may comprise various organic and/or inorganic pigments (in addition to those found in the spherule), alone or in combination with one or more non-pigmentatious powders.

The organic pigments are generally various aromatic types including azo, indigoid, triphenylmethane, anthraquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof.

The composition may contain a mixture of both pigmentatious and non-pigmentatious particulate matter. The percentage of pigment used in the particulate matter component will depend on the type of cosmetic being formulated. Preferred is where the particulate phase comprises a mixture of pigmentitious and non-pigmentitious particulate matter, generally ranging from about 0.1-80% pigmentitious particulate matter to about 0.1-90% non-pigmentitious particulate.

5. Thickening Agents

It may be desirable to include one or more thickening agents in the compositions. Thickening may be achieved by waxes or monmorillonite minerals, or various types of associative thickeners. If present, suggested ranges of thickening agent are from about 0.01-75%, preferably about 0.1-65%, more preferably about 0.5-50% by weight of the total composition.

Suitable waxes include animal, vegetable, mineral, and synthetic waxes, or silicone waxes. Generally such waxes have a melting point ranging from about 28 to 125° C., preferably about 30 to 100° C. Examples of waxes include acacia, beeswax, ceresin, flower wax, citrus wax, carnauba wax, jojoba wax, japan wax, polyethylene, microcrystalline, rice bran, lanolin wax, mink, montan, bayberry, ouricury, ozokerite, palm kernel wax, paraffin, avocado wax, apple wax, shellac wax, clary wax, spent grain wax, candelilla, grape wax, and polyalkylene glycol derivatives thereof such as PEG 6-20 beeswax, or PEG-12 carnauba wax.

Also suitable are various types of silicone waxes, referred to as alkyl silicones, which are polymers that comprise repeating dimethylsiloxy units in combination with one or more methyl-long chain alkyl siloxy units wherein the long chain alkyl is generally a fatty chain that provides a wax-like characteristic to the silicone. Such silicones include, but are not limited to stearoxydimethicone, behenoxy dimethicone, stearyl dimethicone, cetearyl dimethicone, and so on.

Suitable waxes are also set forth in U.S. Pat. No. 5,725,845 which is hereby incorporated by reference in its entirety.

If present, suitable montmorillonite minerals include natural or synthetic montmorillonite minerals such as hectorite, bentonite, and quaternized derivatives thereof which are obtained by reacting the minerals with a quaternary ammonium compound, such as stearalkonium bentonite, hectorites, quaternized hectorites such as Quaternium-18 hectorite, attapulgite, and bentones, either alone or in combination with carbonate activators such as propylene carbonate.

Other types of thickening agents include fatty acids or alcohols, optionally substituted with hydroxyl groups, for example 12-hydroxystearic acid. Such fatty acids or alcohols have the general formula R—COOH or R—OH respectively, where R is a straight or branched chain, saturated or unsaturated alkyl having from about 6 to 45 carbon atoms, wherein one or more of the alkyl groups may be substituted with functional groups such as hydroxy, alkoxy, alkyl, and so on.

6. Surfactants

If present, the surfactant may range from about 0.001-40%, preferably about 0.1-15%, more preferably about 0.5-10% by weight of the total composition. The surfactant may be in the nonionic, cationic, anionic, zwitterionic, or amphoteric form. Preferably, if surfactants are present they are nonionic.

(a). Nonionic Organic Surfactants

Suitable nonionic surfactants include alkoxylated alcohols, or ethers, formed by the reaction of an alcohol with an alkylene oxide, usually ethylene or propylene oxide. Preferably the alcohol is a fatty alcohol having 6 to 30 carbon atoms. Examples of such ingredients include Beheneth 5-30, which is formed by the reaction of behenyl alcohol and ethylene oxide where the number of repeated ethylene oxide units ranges from 5 to 30; Ceteareth 2-100, formed by the reaction of a mixture of cetyl and stearyl alcohol with ethylene oxide, where the number of repeating ethylene oxide units in the molecule ranges from 2 to 100; Ceteth 1-45 which is formed by the reaction of cetyl alcohol and ethylene oxide, and the number of repeating ethylene oxide units ranges from 1 to 45, and so on. Other alkoxylated alcohols are formed by the reaction of fatty acids, mono-, di- or polyhydric alcohols, and alkylene oxides. For example, compounds formed by the reaction of $C_{6-30}$ fatty carboxylic acids, polyhydric alcohols (such as monosaccharides such as glucose, galactose, glycerin, methyl glucose) and an alkoxylated alcohol (such as steareth, beheneth, ceteareth, and the like) are also suitable.

Also suitable as the nonionic surfactant are alkyoxylated carboxylic acids, which are formed by the reaction of a carboxylic acid with an alkylene oxide or with a polymeric ether. The resulting products have the general formula:

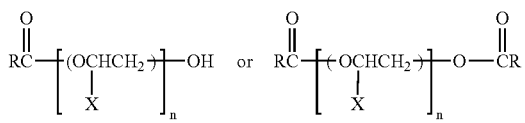

where R is a $C_{1-30}$ straight or branched chain saturated or unsaturated alkyl, X is hydrogen or lower alkyl, and n is the number of polymerized alkoxy groups, which may range from 2 to 100,000. In the case of the diesters, the two RCO— groups do not need to be identical.

Also suitable as the nonionic surfactant are monomeric, homopolymeric and block copolymeric ethers. Such ethers are formed by the polymerization of monomeric alkylene oxides, generally ethylene or propylene oxide. Such polymeric ethers have the following general formula:

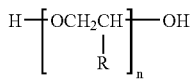

wherein R is H or lower alkyl and n is the number of repeating monomer units, and ranges from 1 to 500.

Other suitable nonionic surfactants include alkoxylated sorbitan and alkoxylated sorbitan derivatives. For example, alkoxylation, in particular, ethoxylation, of sorbitan provides polyalkoxylated sorbitan derivatives. Esterification of polyalkoxylated sorbitan provides sorbitan esters such as the polysorbates. Examples of such ingredients include Polysorbates 20-85, sorbitan oleate, sorbitan palmitate, sorbitan sesquiisostearate, sorbitan stearate, and so on.

Also, particularly suitable as nonionic organic surfactants are various types of esters of fatty acids and glycerin or polyglycerin. Examples of such fatty acid esters include glyceryl stearate, diglyceryl diiosostearate, polyglyceryl-3-isostearate, polyglyceryl-4 isostearate, polyglyceryl-6 ricinoleate, polyglyceryl-4-diisostearate, glyceryl dioleate, glyceryl diisotearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

(b). Silicone Surfactants

Suitable silicone surfactants include those that have a polymeric backbone having siloxy units that have linear repeating units, e.g. di(lower)alkylsiloxy units, preferably dimethylsiloxy units. The silicone surfactant has a hydrophilic portion, which is generally achieved by substitution onto the polymeric backbone of a radical that confers hydrophilic properties to a portion of the molecule. The hydrophilic radical may be substituted on a terminus of the silicone, or on any one or more repeating units of the polymer. In general, the repeating dimethylsiloxy units of modified polydimethylsiloxane surfactants are lipophilic in nature due to the methyl groups, which confer lipophilicity to the molecule. In addition, longer chain alkyl radicals, hydroxy-polypropyleneoxy radicals, or other types of lipophilic radicals may be substituted onto the siloxy backbone to confer further lipophilicity and organocompatibility. If the lipophilic portion of the molecule is due in whole or part to a specific radical, this lipophilic radical may be substituted on a terminus of the organosilicone polymer, or on any one or more repeating units of the polymer. It should also be understood that the silicone surfactant, if used in the compositions of the invention, should have at least one hydrophilic portion and one lipophilic portion.

The term "hydrophilic radical" means a radical that, when substituted onto the silicone polymer backbone, confers hydrophilic properties to the substituted portion of the polymer. Examples of radicals that will confer hydrophilicity are hydroxy-polyethyleneoxy, hydroxyl, carboxylates, sulfonates, sulfates, phosphates, or amines.

The term "lipophilic radical" means an organic radical that, when substituted onto the silicone polymer backbone, confers lipophilic properties to the substituted portion of the polymer. Examples of organic radicals that will confer lipophilicity are $C_{1-40}$ straight or branched chain alkyl, fluoro, aryl, aryloxy, $C_{1-40}$ hydrocarbyl acyl, hydroxy-polypropyleneoxy, or mixtures thereof. The $C_{1-40}$ alkyl may be non-interrupted, or interruped by one or more oxygen atoms, a benzene ring, amides, esters, or other functional groups.

The silicone surfactants may have the following general formula:

I.

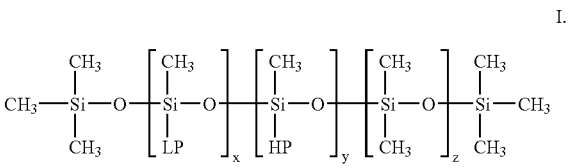

II.

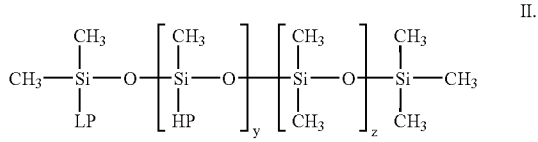

-continued

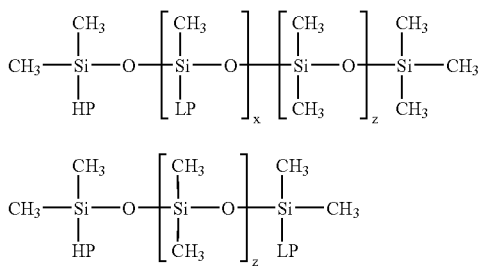

wherein LP is a lipophilic radical
HP is a hydrophilic radical
x is 0-5000
y is 0-5000, and
z is 0-5000, with the proviso that the organosiloxane contains at least on hydrophilic radical and at least one lipophilic radical.

More preferred are compounds of the generic formula I, above, wherein LP is a lipophilic radical which is a $C_{1-40}$ straight or branched chain alkyl, HP is a hydrophilic radical containing hydroxy-polyethyleneoxy. Most preferred is a compound of the formula:

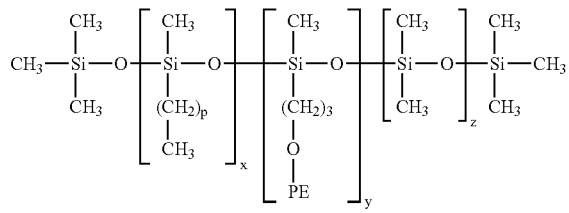

wherein p is 10-40, preferably 12-20, most preferably 15, a is 1-50,000, b is 1-50,000, and PE is $(-C_2H_4O)_a(-C_3H_6O)_b-H$ where x, y, z, a, and b are such that the maximum molecular weight of the polymer is approximately 50,000. Silicone surfactants useful in the compositions of the invention are commercially available from Goldschmidt Corporation under the ABIL tradename. One type of such surfactant is cetyl dimethicone copolyol and has the tradename ABIL WE 09 or ABIL WS 08. The cetyl dimethicone copolyol may be used alone or in conjunction with other non-silicone organic surfactants. For example, the cetyl dimethicone copolyol may be in a mixture with other non-silicone organic surfactants and emollients. In particular, blends of 25-50% of the organosiloxane surfactant, 25-50% of a non-silicone organic surfactant, and 25-50% by weight emollients or oils are preferred. For example, the mixtures identified by the C.T.F.A. names cetyl dimethicone copolyol (and) polyglyceryl 4-isostearate (and) hexyl laurate, or cetyl dimethicone copolyol (and) polyglyceryl-3 oleate (and) hexyl laurate both work well. These blends contain approximately 25-50% of each ingredient, for example ABIL WE 09 contains approximately, by weight of the total ABIL composition, 25-50% cetyl dimethicone copolyol, 25-50%, polyglyceryl 4-isostearate, and 25-50% of hexyl laurate which is an emollient or oil.

Another type of silicone surfactant suitable for use in the compositions of the invention are sold by Union Carbide under the Silwet™ trademark. These surfactants are represented by the following generic formulas:

wherein
PE=-(EO)$_m$(PO)$_n$R
R=lower alkyl or hydrogen
Me=methyl
EO is polyethyleneoxy
PO is polypropyleneoxy
m and n are each independently 1-5000
x and y are each independently 0-5000, and

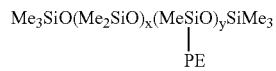

wherein
PE=—CH$_2$CH$_2$CH$_2$O(EO)$_m$(PO)$_n$Z
Z=lower alkyl or hydrogen, and
Me, m, n, x, y, EO and PO are as described above, with the proviso that the molecule contains a lipophilic portion and a hydrophilic portion. Again, the lipophilic portion can be supplied by a sufficient number of methyl groups on the polymer backbone.

One particular type of silicone surfactant is sold under the Silwet™ brand and has the following general formula:

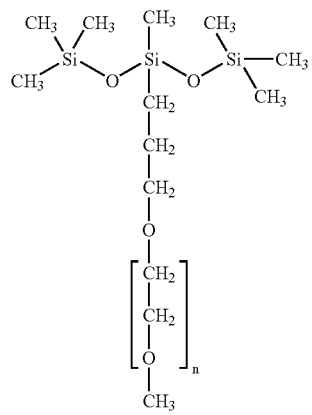

wherein n is 1-10, preferably 8.

Generally silicone co-emsulfiers suitable for use in the compositions of the invention are known by the INCI name dimethicone copolyol and cetyl dimethicone copolyol.

Examples of other silicone surfactants include amino/polyoxyalkyleneated polydiorganosiloxanes disclosed in U.S. Pat. No. 5,147,578. Also suitable are organosiloxanes sold by Goldschmidt under the ABIL trademark including ABIL B-9806, as well as those sold by Rhone-Poulenc under the Alkasil tradename. Also, organosiloxane surfactants sold by Amerchol under the Amersil tradename, including Amersil ME-358, Amersil DMC-287 and Amersil DMC-357 are suitable. Dow Corning surfactants such as Dow Corning 3225C Formulation Aid, Dow Corning 190 Surfactant, Dow Corning 193 Surfactant, Dow Corning Q2-5200, and the like are also suitable Suitable cationic, anionic, zwitterionic, and amphoteric surfactants are disclosed in U.S. Pat. No. 5,534,265, which is hereby incorporated by reference in its entirety.

6. Sunscreens

If desired, the compositions of the invention may contain 0.001-20%, preferably 0.01-10%, more preferably 0.05-8% of one or more sunscreens. A sunscreen is defined as an ingredient that absorbs at least 85 percent of the light in the UV range at wavelengths from 290 to 320 nanometers, but transmits UV light at wavelengths longer than 320 nanometers. Sunscreens generally work in one of two ways. Particulate materials, such as zinc oxide or titanium dioxide, as mentioned above, physically block ultraviolet radiation. Chemical sunscreens, on the other hand, operate by chemically reacting upon exposure to UV radiation. Suitable sunscreens that may be included in the compositions of the invention are set forth on pages 1808-1809 of the *CTFA Cosmetic Ingredient Dictionary and Handbook*, Eighth Edition, 2000, as well as U.S. Pat. No. 5,620,965, both of which are hereby incorporated by reference. Further examples of chemical and physical sunscreens include those set forth below.

(a). UVA Chemical Sunscreens

The term "UVA sunscreen" means a chemical compound that blocks UV radiation in the wavelength range of about 320 to 400 nm. Preferred UVA sunscreens are dibenzoylmethane compounds having the general formula:

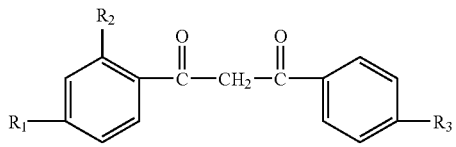

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercial available from Givaudan-Roure under the trademark Parsol 1789, and Merck & Co. under the tradename Eusolex 9020.

If present the sunscreens may be found ranging from about 0.001-20%, preferably 0.005-5%, more preferably about 0.005-3% by weight of the composition of UVA sunscreen.

(b). UVB Chemical Sunscreens

The term "UVB sunscreen" means a compound that blocks UV radiation in the wavelength range of from about 290 to 320 nm. A variety of UVB chemical sunscreens exist including α-cyano-β,β-diphenyl acrylic acid esters as set forth in U.S. Pat. No. 3,215,724, which is hereby incorporated by reference in its entirety. Particularly preferred is Octocrylene, which is 2-ethylhexyl 2-cyano-3,3-diphenylacrylate. Preferred is where the composition contains no more than about 10% by weight of the total composition of octocrylene. Suitable amounts range from about 0.001-10% by weight. Octocrylene may be purchased from BASF under the tradename Uvinul N-539.

Other suitable sunscreens include benzylidene camphor derivatives as set forth in U.S. Pat. No. 3,781,417, which is hereby incorporated by reference in its entirety. Such benzylidene camphor derivatives have the general formula:

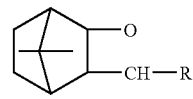

wherein R is p-tolyl or styryl, preferably styryl. Particularly preferred is 4-methylbenzylidene camphor, which is a lipid soluble UVB sunscreen compound sold under the tradename Eusolex 6300 by Merck.

Also suitable are cinnamate derivatives having the general formula:

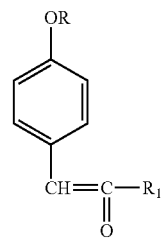

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octoxinate or octyl methoxycinnamate. The compound may be purchased from Givaudan Corporation under the tradename Parsol MCX, or BASF under the tradename Uvinul MC 80. Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at nor more than about 3% by weight of the total composition.

Also suitable as the UVB screening agents are various benzophenone derivatives having the general formula:

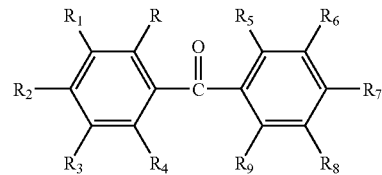

R through $R_9$ are each independently H, OH, $NaO_3S$, $SO_3H$, $SO_3Na$, Cl, R", OR" where R" is $C_{1-20}$ straight or branched chain alkyl. Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone) and Benzophenone 4 (also referred to as Sulisobenzone), Benzophenone 5 (Sulisobenzone Sodium), and the like. Most preferred is Benzophenone 3.

Also suitable are certain menthyl salicylate derivatives having the general formula:

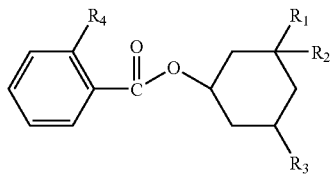

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Homosalate is available commercially from Merck under the tradename Eusolex HMS and menthyl anthranilate is commercially available from Haarmann & Reimer under the tradename Heliopan. If present, the Homosalate should be found at no more than about 15% by weight of the total composition.

Various amino benzoic acid derivatives are suitable UVB absorbers including those having the general formula:

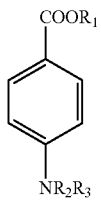

Wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate 0), ethyldihydroxypropyl PABA, and the like. If present Padimate 0 should be found at no more than about 8% by weight of the total composition.

Salicylate derivatives are also acceptable UVB absorbers. Such compounds have the general formula:

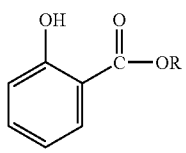

wherein R is a straight or branched chain alkyl, including derivatives of the above compound formed from mono-, di-, or triethanolamines. Particular preferred are octyl salicylate, TEA-salicylcate, DEA-salicylate, and mixtures thereof.

Generally, the amount of the UVB chemical sunscreen present may range from about 0.001-45%, preferably 0.005-40%, more preferably about 0.01-35% by weight of the total composition.

(c). Physical Sunscreens

The composition may also contain one or more physical sunscreens. The term "physical sunscreen" means a material that is generally particulate in form that is able to block UV rays by forming an actual physical block on the skin. Examples of particulates that serve as solid physical sunblocks include titanium dioxide, zinc oxide and the like in particle sizes ranging from about 0.001-50 microns, preferably less than 1 micron.

7. Vitamins and Antioxidants

The compositions of the invention may contain vitamins and/or coenzymes, as well as antioxidants. If so, 0.001-10%, preferably 0.01-8%, more preferably 0.05-5% by weight of the total composition are suggested. Suitable vitamins include ascorbic acid and derivatives thereof, the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also Vitamin A and derivatives thereof are suitable. Examples are Vitamin A palmitate, acetate, or other esters thereof, as well as Vitamin A in the form of beta carotene. Also suitable is Vitamin E and derivatives thereof such as Vitamin E acetate, nicotinate, or other esters thereof. In addition, Vitamins D and K are suitable.

Suitable antioxidants are ingredients that assist in preventing or retarding spoilage. Examples of antioxidants suitable for use in the compositions of the invention are potassium sulfite, sodium bisulfite, sodium erythrobate, sodium metabisulfite, sodium sulfite, propyl gallate, cysteine hydrochloride, butylated hydroxytoluene, butylated hydroxyanisole, and so on.

8. Other Botanical Extracts

It may be desirable to include one or more additional botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including acacia (dealbata, famesiana, senegal), acer saccharinum (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, green tea, chamomile, willowbark, mulberry, poppy, and those set forth on pages 1646 through 1660 of the *CTFA Cosmetic Ingredient Handbook*, Eighth Edition, Volume 2.

9. Other Film Forming Polymers

It may be desired for the cosmetic composition to contain one or more additional film forming polymers. Such polymers may be silicones or polymers with repeating organic moieties. If present, such film forming polymers are found in ranges of about 0.001-50%, preferably about 0.01-45%, more preferably about 0.1-20% by weight of the total composition. Such film forming polymers may be present in the form of dispersed or solvated particles in water, or in other non-aqueous solvents such as paraffinic hydrocarbons, silicone oils, or organic oils. Examples of such film forming polymers include those set forth below.

(a). Copolymers of Silicone and Ethylenically Unsaturated Monomers

One type of film forming polymer that may be used in the compositions of the invention is obtained by reacting silicone moieties with ethylenically unsaturated monomers.

The resulting copolymers may be graft or block copolymers. The term "graft copolymer" is familiar to one of ordinary skill in polymer science and is used herein to describe the copolymers which result by adding or "grafting" polymeric side chain moieties (i.e. "grafts") onto another polymeric moiety referred to as the "backbone". The backbone may have a higher molecular weight than the grafts. Thus, graft copolymers can be described as polymers having pendant polymeric side chains, and which are formed from the "grafting" or incorporation of polymeric side chains onto or into a polymer backbone. The polymer backbone can be a homopolymer or a copolymer. The graft copolymers are derived from a variety of monomer units.

One type of polymer that may be used as the film forming polymer is a vinyl-silicone graft or block copolymer having the formula:

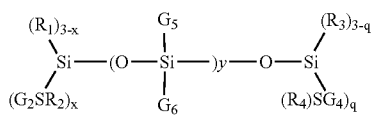

wherein $G_5$ represents monovalent moieties which can independently be the same or different selected from the group consisting of alkyl, aryl, aralkyl, alkoxy, alkylamino, fluoroalkyl, hydrogen, and -ZSA; A represents a vinyl polymeric segment consisting essentially of a polymerized free radically polymerizable monomer, and Z is a divalent linking group such as $C_{1-10}$ alkylene, aralkylene, arylene, and alkoxylalkylene, most preferably Z is methylene or propylene.

$G_6$ is a monovalent moiety which can independently be the same or different selected from the group consisting of alkyl, aryl, aralkyl, alkoxy, alkylamino, fluoroalkyl, hydrogen, and -ZSA;

$G_2$ comprises A;

$G_4$ comprises A;

$R_1$ is a monovalent moiety which can independently be the same or different and is selected from the group consisting of alkyl, aryl, aralkyl, alkoxy, alkylamino, fluoroalkyl, hydrogen, and hydroxyl; but preferably $C_{1-4}$ alkyl or hydroxyl, and most preferably methyl.

$R_2$ is independently the same or different and is a divalent linking group such as $C_{1-10}$ alkylene, arylene, aralkylene, and alkoxyalkylene, preferably $C_{1-3}$ alkylene or $C_{7-10}$ aralkylene, and most preferably —$CH_2$— or 1,3-propylene, and $R_3$ is a monovalent moiety which is independently alkyl, aryl, aralkyl, alkoxy, alkylamino, fluoroalkyl, hydrogen, or hydroxyl, preferably $C_{1-4}$ alkyl or hydroxyl, most preferably methyl;

$R_4$ is independently the same or different and is a divalent linking group such as $C_{1-10}$ alkylene, arylene, aralkylene, alkoxyalkylene, but preferably $C_{1-3}$ alkylene and $C_{7-10}$ alkarylene, most preferably —$CH_2$— or 1,3-propylene.

x is an integer of 0-3;

y is an integer of 5 or greater; preferably 10 to 270, and more preferably 40-270; and q is an integer of 0-3.

These polymers are described in U.S. Pat. No. 5,468,477, which is hereby incorporated by reference. Most preferred is poly(dimethylsiloxane)-g-poly(isobutyl methacrylate), which is manufactured by 3-M Company under the tradename VS 70 IBM. This polymer may be purchased in the dry particulate form, or as a solution where the polymer is dissolved or dispersed in one or more of the liquids that may be found in the composition such as volatile oils (isododecane), water, or other non-volatile or volatile oils. Preferred is where the polymer is in dry particulate form, and as such it can be dissolved in one or more of the liquids comprising the liquid carrier. This polymer has the CTFA name Polysilicone-6.

Another type of such a polymer comprises a vinyl, methacrylic, or acrylic backbone with pendant siloxane groups and pendant fluorochemical groups. Such polymers preferably comprise comprise repeating A, C, D and optionally B monomers wherein:

A is at least one free radically polymerizable acrylic or methacrylic ester of a 1,1,-dihydroperfluoroalkanol or analog thereof, omega-hydridofluoroalkanols, fluoroalkylsulfonamido alcohols, cyclic fluoroalkyl alcohols, and fluoroether alcohols, B is at least one reinforcing monomer copolymerizable with A, C is a monomer having the general formula X(Y)nSi(R) 3-m Z.m wherein X is a vinyl group copolymerizable with the A and B monomers, Y is a divalent linking group which is alkylene, arylene, alkarylene, and aralkylene of 1 to 30 carbon atoms which may incorporate ester, amide, urethane, or urea groups, n is zero or 1;

m is an integer of from 1 to 3,

R is hydrogen, $C_{1-4}$ alkyl, aryl, or alkoxy,

Z is a monovalent siloxane polymeric moiety; and

D is at least one free radically polymerizable acrylate or methacrylate copolymer.

Such polymers and their manufacture are disclosed in U.S. Pat. Nos. 5,209,924 and 4,972,037, which are hereby incorporated by reference.

More specifically, the preferred polymer is a combination of A, C, and D monomers wherein A is a polymerizable acrylic or methacrylic ester of a fluoroalkylsulfonamido alcohol, and where D is a methacrylic acid ester of a $C_{1-2}$ straight or branched chain alcohol, and C is as defined above. Most preferred is a polymer having moieties of the general formula:

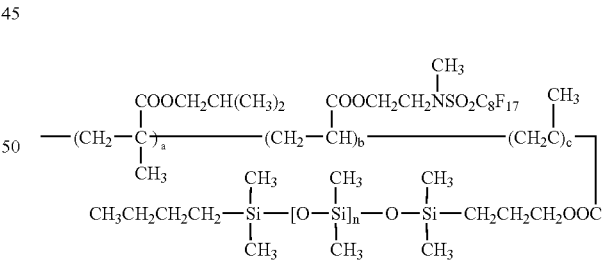

wherein each of a, b, and c has a value in the range of 1-100,000, and the terminal groups are selected from the group consisting of a $C_{1-20}$ straight or branched chain alkyl, aryl, and alkoxy and the like. These polymers may be purchased from Minnesota Mining and Manufacturing Company under the tradenames "Silicone Plus" polymers. Most preferred is poly(isobutyl methacrylate-co-methyl FOSEA)-g-poly(dimethylsiloxane) which is sold under the tradename SA 70-5 IBMMF.

Another suitable silicone acrylate copolymer is a polymer having a vinyl, methacrylic, or acrylic polymeric backbone with pendant siloxane groups. Such polymers as disclosed in U.S. Pat. Nos. 4,693,935, 4,981,903, 4,981,902, and which are hereby incorporated by reference. Preferably, these polymers are comprised of A, C, and optionally B monomers wherein:

A is at least on free radically polymerizable vinyl, methacrylate, or acrylate monomer;

B, when present, is at least one reinforcing monomer copolymerizable with A,

C is a monomer having the general formula:

wherein:

X is a vinyl group copolymerizable with the A and B monomers;

Y is a divalent linking group;

n is zero or 1;

m is an integer of from 1 to 3;

R is hydrogen, $C_{1-10}$ alkyl, substituted or unsubstituted phenyl, $C_{1-10}$ alkoxy; and Z is a monovalent siloxane polymeric moiety.

Examples of A monomers are lower to intermediate methacrylic acid esters of $C_{1-12}$ straight or branched chain alcohols, styrene, vinyl esters, vinyl chloride, vinylidene chloride, acryloyl monomers, and so on.

The B monomer, if present, is a polar acrylic or methacrylic monomer having at least one hydroxyl, amino, or ionic group (such as quaternary ammonium, carboxylate salt, sulfonic acid salt, and so on).

The C monomer is as above defined.

Examples of other suitable copolymers that may be used herein, and their method of manufacture, are described in detail in U.S. Pat. No. 4,693,935, Mazurek, U.S. Pat. No. 4,728,571, and Clemens et al., both of which are incorporated herein by reference. Additional grafted polymers are also disclosed in EPO Application 90307528.1, published as EPO Application 0 408 311, U.S. Pat. No. 5,061,481, Suzuki et al., U.S. Pat. No. 5,106,609, Bolich et al., U.S. Pat. No. 5,100,658, Bolich et al., U.S. Pat. No. 5,100,657, Ansher-Jackson, et al., U.S. Pat. No. 5,104,646, Bolich et al., U.S. Pat. No. 5,618,524, issued Apr. 8, 1997, all of which are incorporated by reference herein in their entirety.

(b). Polymers from Ethylenically Unsaturated Monomers

Also suitable for use as film forming polymers are polymers made by polymerizing one or more ethylenically unsaturated monomers. The final polymer may be a homopolymer, copolymer, terpolymer, or graft or block copolymer, and may contain monomeric units such as acrylic acid, methacrylic acid or their simple esters, styrene, ethylenically unsaturated monomer units such as ethylene, propylene, butylene, etc., vinyl monomers such as vinyl chloride, styrene, and so on.

Preferred are polymers containing one or more monomers which are esters of acrylic acid or methacrylic acid, including aliphatic esters of methacrylic acid like those obtained with the esterification of methacrylic acid or acrylic acid with an aliphatic alcohol of 1 to 30, preferably 2 to 20, more preferably 2 to 8 carbon atoms. If desired, the aliphatic alcohol may have one or more hydroxy groups. Also suitable are methacrylic acid or acrylic acid esters esterified with moieties containing alicyclic or bicyclic rings such as cyclohexyl or isobornyl, for example.

The ethylenically unsaturated monomer may be mono-, di-, tri-, or polyfunctional as regards the addition-polymerizable ethylenic bonds. A variety of ethylenically unsaturated monomers are suitable.

Examples of suitable monofunctional ethylenically unsaturated monomers include those of the formula:

wherein $R_1$ is H, a $C_{1-30}$ straight or branched chain alkyl, aryl, aralkyl; $R_2$ is a pyrrolidone, a $C_{1-30}$ straight or branched chain alkyl, or a substituted or unsubstituted aromatic, alicyclic, or bicyclic ring where the substitutents are $C_{1-30}$ straight or branched chain alkyl, or COOM wherein M is H, a $C_{1-30}$ straight or branched chain alkyl, pyrrolidone, or a substituted or unsubstituted aromatic, alicyclic, or bicyclic ring where the substitutents are $C_{1-30}$ straight or branched chain alkyl which may be substituted with one or more hydroxyl groups, or $[(CH_2)_mO]_nH$ wherein m is 1-20, and n is 1-200.

Preferably, the monofunctional ethylenically unsaturated monomer is of Formula I, above, wherein $R_1$ is H or a $C_{1-30}$ alkyl, and $R_2$ is COOM wherein M is a $C_{1-30}$ straight or branched chain alkyl which may be substituted with one or more hydroxy groups.

More preferably, $R_1$ is H or $CH_3$, and $R_2$ is COOM wherein M is a $C_{1-10}$ straight or branched chain alkyl which may be substituted with one or more hydroxy groups. In the preferred embodiment of the invention, the monofunctional ethylenically unsaturated monomer is a mixture of monomers of Formula I where in one monomer $R_1$ is H or $CH_3$ and $R_2$ is COOM where M is a $C_{1-10}$ alkyl, and where in the second monomer $R_1$ is H or $CH_3$, and $R_2$ is COOM where M is a $C_{1-10}$ alkyl substituted with one or more hydroxy groups.

Di-, tri- and polyfunctional monomers, as well as oligomers, of the above monofunctional monomers may also be used to form the polymer. Suitable difunctional monomers include those having the general formula:

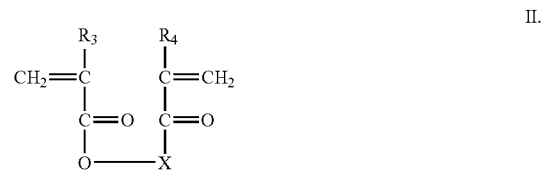

wherein $R_3$ and $R_4$ are each independently H, a $C_{1-30}$ straight or branched chain alkyl, aryl, or aralkyl; and X is $[(CH_2)_x O_y]_z$ wherein x is 1-20, and y is 1-20, and z is 1-100. Particularly preferred are difunctional acrylates and methacrylates, such as the compound of formula II above wherein $R_3$ and $R_4$ are $CH_3$ and X is $[(CH_2)_xO_y]_z$ wherein x is 1-4; and y is 1-6; and z is 1-10.

Trifunctional and polyfunctional monomers are also suitable for use in the polymerizable monomer to form the polymer used in the compositions of the invention. Examples of such monomers include acrylates and methacrylates such as trimethylolpropane trimethacrylate or trimethylolpropane triacrylate.

The polymers can be prepared by conventional free radical polymerization techniques in which the monomer, solvent, and polymerization initiator are charged over a 1-24 hour period of time, preferably 2-8 hours, into a conventional polymerization reactor in which the constituents are heated to about 60-175° C., preferably 80-100° C. The polymers may also be made by emulsion polymerization or suspension polymerization using conventional techniques. Also anionic polymerization or Group Transfer Polymerization (GTP) is another method by which the copolymers used in the invention may be made. GTP is well known in the art and disclosed in U.S. Pat. Nos. 4,414,372; 4,417,034; 4,508,880; 4,524,196; 4,581,428; 4,588,795; 4,598,161; 4,605,716; 4,605,716; 4,622,372; 4,656,233; 4,711,942; 4,681,918; and 4,822,859; all of which are hereby incorporated by reference.

Also suitable are polymers formed from the monomer of Formula I, above, which are cyclized, in particular, cycloalkylacrylate polymers or copolymers having the following general formulas:

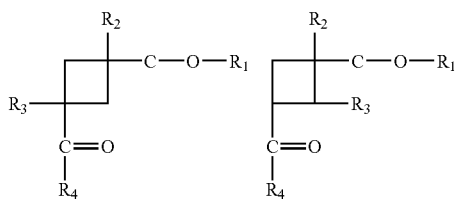

wherein $R_1$, $R_2$, $R_3$, and $R_4$ are as defined above. Typically such polymers are referred to as cycloalkylacrylate polymers. Such polymers are sold by Phoenix Chemical, Inc. under the tradename Giovarez AC-5099M. Giovarez has the chemical name isododecane acrylates copolymer and the polymer is solubilized in isododecane. The monomers mentioned herein can be polymerized with various types of organic groups such as propylene glycol, isocyanates, amides, etc.

One type of organic group that can be polymerized with the above monomers includes a urethane monomer. Urethanes are generally formed by the reaction of polyhydroxy compounds with diisocyanates, as follows:

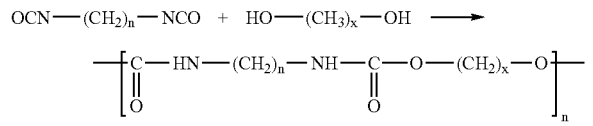

wherein x is 1-1000.

Another type of monomer that may be polymerized with the above comprise amide groups, preferably having the the following formula:

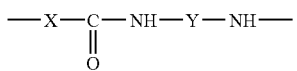

wherein X and Y are each independently linear or branched alkylene having $_{1-40}$ carbon atoms, which may be substituted with one or more amide, hydrogen, alkyl, aryl, or halogen substituents.

Another type of organic monomer may be alpha or beta pinenes, or terpenes, abietic acid, and the like.

(c). Silicone Polymers

Also suitable are various types of high molecular weight silicone polymers including those having the formula set forth below:

wherein R, R' and R" are each independently a $C_{1-10}$ straight or branched chain alkyl or phenyl, and x and y are such that the ratio of $(RR'R")_3SiO_{1/2}$ units to $SiO_2$ units is 0.5 to 1 to 1.5 to 1.

Preferably R, R' and R" are a $C_{1-6}$ alkyl, and more preferably are methyl and x and y are such that the ratio of $(CH_3)_3SiO_{1/2}$ units to $SiO_2$ units is 0.75 to 1. Most preferred is this trimethylsiloxy silicate containing 2.4 to 2.9 weight percent hydroxyl groups, which is formed by the reaction of the sodium salt of silicic acid, chlorotrimethylsilane, and isopropyl alcohol. The manufacture of trimethylsiloxy silicate is set forth in U.S. Pat. Nos. 2,676,182; 3,541,205; and 3,836,437, all of which are hereby incorporated by reference. Trimethylsiloxy silicate as described is available from Dow Corning Corporation under the tradename 749 Fluid (formerly known as 2-0749), which is a blend of about 40-60% volatile silicone and 40-60% trimethylsiloxy silicate. Dow Corning 749 Fluid in particular, is a fluid containing about 50% trimethylsiloxy silicate and about 50% cyclomethicone. The fluid has a viscosity of 200-700 centipoise at 25° C., a specific gravity of 1.00 to 1.10 at 25° C., and a refractive index of 1.40-1.41. A similar siloxysilicate resin is available from GE Silicones under the tradename SR1000 and is a fine particulate solid material.

Another type of silicone polymer suitable for use in the invention comprises the silicone esters set forth in U.S. Pat. No. 5,725,845, which is hereby incorporated by reference in its entirety. Other polymers that can enhance adhesion to skin include silicone esters comprising units of the general formula $R_aR^E{}_bSiO_{[4-(a+b)/2]}$ or $R^{13}{}_xR^E{}_ySiO_{1/2}$ wherein R and $R^{13}$ are each independently an organic radical such as alkyl, cycloalkyl, or aryl, or, for example, methyl, ethyl, propyl, hexyl, octyl, decyl, aryl, cyclohexyl, and the like, a is a number ranging from 0 to 3, b is a number ranging from 0 to 3, a+b is a number ranging from 1 to 3, x is a number from 0 to 3, y is a number from 0 to 3 and the sum of x+y is 3, and wherein $R^E$ is a carboxylic ester containing radical. Preferred $R_E$ radicals are those wherein the ester group is formed of one or more fatty acid moieities (e.g. of about 2, often about 3 to 10 carbon atoms) and one or more aliphatic alcohol moieities (e.g. of about 10 to 30 carbon atoms). Examples of such acid moieities include those derived from branched-chain fatty acids such as isostearic, or straight chain fatty acids such as behenic. Examples of suitable alcohol moieties include those derived from monohydric or polyhydric alcohols, e.g. normal alkanols such as n-propanol and branched-chain etheralkanols such as (3,3,3-trimethylolpropoxy)propane. Preferably the ester subgroup (i.e. the carbonyloxy radical) will be linked to the silicon atom by a divalent aliphatic chain that is at least 2 or 3 carbon atoms in length, e.g. an alkylene group or a divalent alkyl ether group. Most preferably that chain will be part of the alcohol moiety, not the acid moiety.

Preferably the silicone ester will have a melting point of no higher than about 120° C. It can be a liquid or solid at room temperature. Preferably it will have a waxy feel and a molecular weight of no more than about 100,000 daltons.

Silicone esters having the above formula are disclosed in U.S. Pat. No. 4,725,658 and U.S. Pat. No. 5,334,737, which are hereby incorporated by reference. Specific types of silicone esters include liquid siloxy silicates disclosed in U.S. Pat. No. 5,334,737, e.g. diisostearoyl trimethylolpropane siloxysilicate (prepared in Examples 9 and 14 of this patent), and dilauroyl trimethylolpropane siloxy silicate (prepared in Example 5 of the patent), which are commercially available from General Electric under the tradenames SF 1318 and SF 1312, respectively.

Silicone gums or other types of silicone solids may be used provided they are soluble in the liquid vehicle. Examples of silicone gums include those set forth in U.S. Pat. No. 6,139,823, which is hereby incorporated by reference. Preferred gums have a 600,000 to 1,000,000 centipoise at 25° C.

(d). Natural Polymers

Also suitable for use are one or more naturally occuring polymeric materials such as resinous plant extracts including such as rosin, shellac, and the like.

The compositions may be in the form of foundation makeup, powder, blush, concealer, eye shadow, eyeliner, mascara, lipstick, lipliner, and the like. The cosmetic compositions may be found in the stick, cake, cream, liquid, or semi-solid form, and may be anhydrous or in the emulsion form. In general, foundation makeups are in the water and oil emulsion form and comprise from about 0.1-99% water and 0.1-99% oil, from about 0.1-75% pigments and particulates, and 0.1-99% spherules. Suitable powders are typically in the anhydrous form and comprise from about 0.1-99% powders and pigments, 0.1-80% oil, 0.1-75% thickening agent, and 0.1-99% spherules. Suitable blushes generally comprise from about 0.1-95% pigments and particulates, 0.1-80% oil, 0.1-75% thickening agent and 0.1-99% spherules. Suitable concealers may be in the emulsion or anhydrous form. If in the emulsion form, the ingredients are similar to those found in foundation makeup compositions. If in the anhydrous form, the ingredients and percentage ranges are similar to those found in blushes. Suitable eye shadows may comprise from about 0.1-95% particulates or pigments, 0.1-80% oil, 0.1-75% thickening agent, and 0.1-99% spherules. Suitable eyeliner and mascara formulas may be anhydrous or in the emulsion form, and typically comprise from about 0.1-80% film forming polymer, 0.1-75% oil, and 0.1-75% of pigments and particulates. Suitable lipstick compositions comprise from about 0.1-75% thickening agent, 0.1-80% oil, and 0.1-80% pigments or particulates.

II. The Method

The invention is further directed to a color cosmetic composition containing rupturable synthetic thermoplastic spherules impregnated with color and use of such composition to color skin and to a method for applying color to skin comprising treating the skin with a cosmetic composition containing color impregnated spherules which express color onto the skin when the composition is applied thereto.

The color cosmetic compositions may be in the form of foundation makeup, blush, concealer, eyeshadow, lipstick, eyeliner, mascara, lipliner, and so on. When the color cosmetic composition is applied, the colorant found within the spherules is expressed onto skin either when the spherule ruptures or because the colorant is expressed from the spherule upon application of pressure typically used when the composition is applied to skin. The color is expressed either in whole or in part from the spherule, leaving a spherule where the contents have been at least partially removed. The emptied spherule may be capable of performing an uptake function on the keratinous surface. For example, sebum, perspiration, or similar skin exudates may collect in the spherule on the skin surface, with the net effect being to absorb such skin exudates from the skin surface into the spherules and provide an oil or perspiration blotting function to the composition.

The invention will be further described in connection with the following examples which are set forth for the purposes of illustration only.

EXAMPLE 1

A foundation makeup formula was made as follows:

| Ingredient | % by weight |
| --- | --- |
| Dimethicone 10 cs | 0.70 |
| Cetyl dimethicone copolyol | 1.50 |
| Polyglyceryl-4-isostearate | 1.50 |
| Cyclomethicone, dimethicone | 3.90 |
| Cyclomethicone, trimethylsiloxysilicate | 2.50 |
| Tribehenin | 010 |
| Water | QS |
| Methyl paraben | 0.25 |
| Propyl paraben/laureth-7 | 0.75 |
| Butylene glycol | 4.77 |
| Magnesium ascorbyl phosphate | 0.01 |
| Tetrasodium EDTA | 0.01 |
| *Aloe barbadensis* leaf juice | 0.01 |
| Magnesium sulfate | 1.00 |
| Glycerin | 2.00 |
| Sodium hyaluronate, hydrolyzed glycosaminoglycans | 0.30 |
| Sodium hydroxide | 0.05 |
| Kinetin | 0.05 |
| Dimethicone, cyclomethicone | 15.71 |
| Cyclomethicone, *gingko biloba* extract, *panax ginseng* root extract, *camellia sinensis* leaf extract, *centaurea cyanus* flower extract, *vitis vinefera* seed extract | 0.50 |
| Cyclomethicone, dimethiconol | 2.00 |
| Tocopheryl acetate | 0.01 |
| Retinyl palmitate | 0.01 |
| Cyclomethicone, *glycyrrhiza glabra* root extract | 1.00 |
| *Anthemis noblis* extract | 0.02 |
| Cyclomethicone | 0.50 |
| Dimethicone 10 cs | 1.00 |
| Mica, methicone | 1.89 |
| Titanium dioxide, iron oxides | 0.30 |
| Iron oxides, acrylonitrile methacrylonitrile methylmethacrylate copolymer | 1.00 |
| Titanium dioxide, cyclomethicone, dimethicone copolyol, polyglyceryl-6-ricinoleate, stearic acid, aluminum hydroxide | 13.50 |
| Zinc oxide, cyclomethicone, dimethicone copolyol | 3.50 |
| Titanium dioxide, cyclomethicone, dimethicone copolyol, triethoxycaprylylsilane | 5.00 |
| Iron oxides/methicone (50:50) | 1.85 |
| Nylon-12 | 1.25 |
| Boron nitride | 1.87 |
| Silica | 0.20 |

The composition was prepared by grinding the pigments and powders in a portion of the oils. The remaining oily ingredients were combined and mixed with the water phase ingredients. The spherules were added and mixed well with the composition.

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims.

We claim:

1. A color cosmetic composition containing color impregnated spherules, wherein the color impregnated in the spherule is one or more iron oxides solvated in water and the spherule is comprised of a copolymer of acrylonitrile, methacrylonitrile and methyl methacrylate, and the color is expressed from the spherule upon application of the cosmetic to the keratinous surface and the expressed spherule serves an uptake function on the keratinous surface.

* * * * *